US011707342B2

(12) United States Patent
Harrison et al.

(10) Patent No.: US 11,707,342 B2
(45) Date of Patent: Jul. 25, 2023

(54) IDENTIFICATION SYSTEM FOR MEDICAL DEVICES

(71) Applicant: Medtronic, Inc., Minneapolis, MN (US)

(72) Inventors: Robert Harrison, Milton (CA); Kathryn Atwell, Etobicoke (CA); Michael Same, Toronto (CA); Aaron Kang-Lun Peng, Surrey (CA); Matthew Dawson, Toronto (CA); Gregory Pollieri, Toronto (CA)

(73) Assignee: Medtronic, Inc., Minneapolis, MN (US)

( * ) Notice: Subject to any disclaimer, the term of this patent is extended or adjusted under 35 U.S.C. 154(b) by 634 days.

(21) Appl. No.: 16/472,093

(22) PCT Filed: Dec. 20, 2017

(86) PCT No.: PCT/IB2017/058234
§ 371 (c)(1),
(2) Date: Jun. 20, 2019

(87) PCT Pub. No.: WO2018/116222
PCT Pub. Date: Jun. 28, 2018

(65) Prior Publication Data
US 2020/0085531 A1 Mar. 19, 2020

Related U.S. Application Data

(60) Provisional application No. 62/438,305, filed on Dec. 22, 2016.

(51) Int. Cl.
| A61B 18/12 | (2006.01) |
| A61B 90/92 | (2016.01) |
| A61B 34/00 | (2016.01) |
| A61B 90/94 | (2016.01) |
| A61B 18/14 | (2006.01) |

(Continued)

(52) U.S. Cl.
CPC .......... *A61B 90/92* (2016.02); *A61B 18/1206* (2013.01); *A61B 18/14* (2013.01);
(Continued)

(58) Field of Classification Search
CPC ..... A61B 18/02; A61B 18/1206; A61B 18/14; A61B 18/1477; A61B 2017/00119;
(Continued)

(56) References Cited

U.S. PATENT DOCUMENTS 5,334,181 A * 8/1994 Rubinsky ............... A61B 18/02
606/22
5,342,356 A * 8/1994 Ellman .................. A61B 18/14
606/32
(Continued)

FOREIGN PATENT DOCUMENTS

JP 2001095763 A 4/2001

OTHER PUBLICATIONS

International Search Report and Written Opinion of International Application No. PCT/IB2017/058234, dated Apr. 13, 2018, 30 pp.

*Primary Examiner* — Michael F Peffley
(74) *Attorney, Agent, or Firm* — Shumaker & Sieffert, P.A.

(57) ABSTRACT

A system and method of use thereof are disclosed, the system including a treatment source, such as an electrosurgical generator and a plurality of treatment devices operable to be coupled to the treatment source, one or more of the treatment devices being associated with one or more device identifiers which can be, for example, physically present on the device or contained in device software.

31 Claims, 1 Drawing Sheet

(51) Int. Cl.
  *A61B 18/02* (2006.01)
  *A61B 17/00* (2006.01)
  *A61B 18/00* (2006.01)

(52) U.S. Cl.
  CPC .............. *A61B 34/25* (2016.02); *A61B 90/94* (2016.02); *A61B 18/02* (2013.01); *A61B 2017/00119* (2013.01); *A61B 2018/00577* (2013.01); *A61B 2018/00809* (2013.01); *A61B 2018/00875* (2013.01); *A61B 2018/00898* (2013.01); *A61B 2018/00994* (2013.01); *A61B 2018/1226* (2013.01)

(58) Field of Classification Search
  CPC ........... A61B 2018/00988; A61B 2018/00577; A61B 2018/00809; A61B 2018/00875; A61B 2018/00989; A61B 2018/00994; A61B 2018/1226; A61B 34/25; A61B 90/90; A61B 90/92; A61B 90/94; A61B 90/96; A61B 90/98
  See application file for complete search history.

(56) References Cited

U.S. PATENT DOCUMENTS

| | | | |
|---|---|---|---|
| 5,573,529 A * | 11/1996 | Haak | A61B 90/92 606/1 |
| 6,165,169 A * | 12/2000 | Panescu | A61B 18/1492 606/1 |
| 6,605,049 B1 * | 8/2003 | Wagner | A61B 90/92 600/585 |
| 6,733,495 B1 * | 5/2004 | Bek | A61B 18/00 606/34 |
| 6,783,523 B2 * | 8/2004 | Qin | A61B 18/00 606/1 |
| 2002/0049464 A1 * | 4/2002 | Donofrio | A61B 17/320068 606/169 |
| 2003/0216732 A1 * | 11/2003 | Truckai | A61B 18/14 606/49 |
| 2008/0033350 A1 | 2/2008 | Wilson et al. | |
| 2008/0077128 A1 * | 3/2008 | Woloszko | A61B 5/015 606/41 |
| 2010/0082022 A1 | 4/2010 | Haley et al. | |
| 2013/0137957 A1 * | 5/2013 | Wood | A61B 1/227 600/391 |
| 2013/0231656 A1 * | 9/2013 | Dunning | A61B 90/90 606/34 |
| 2013/0338652 A1 * | 12/2013 | Weber | A61B 18/203 606/45 |
| 2014/0066927 A1 * | 3/2014 | Brustad | A61B 18/1206 606/41 |
| 2014/0074116 A1 * | 3/2014 | Collins | A61B 90/92 606/130 |

* cited by examiner

IDENTIFICATION SYSTEM FOR MEDICAL DEVICES

TECHNICAL FIELD

The disclosure relates to systems and methods for identification of an individual treatment device from a plurality of devices.

SUMMARY

The problem of determining correspondence between (i.e. matching up) a plurality of treatment devices and channels of a treatment source may be solved by each treatment device having a visual identifier which corresponds with a treatment source channel. Treatment sources include power supplies and fluid sources.

In one broad aspect, embodiments of the present invention comprise a system and method of use thereof, the system including a treatment source, such as an electrosurgical generator and a plurality of treatment devices operable to be coupled to the treatment source, one or more of the treatment devices being associated with a unique visual identifier (Colored light, Alphanumeric ID, symbols, coloured label or component, etc.) which can be physically present on the device or activated, and contained in device software. The visual identifier could be on the handle, cable, hub, connectors, or other component.

As a feature of this aspect, the unique visual identifier is selected from the group consisting of a visual signal such as a light e.g. an LED (light-emitting diode) or a physical means for identification such as a label comprising, for example, alphanumeric text, symbols, or other printed, or etched characters. In some alternative embodiments, the identifier is a word such as name. An example of such an embodiment is a system having four probes identified as Kathryn, Rob, Carolyn, and Michael. Some other alternative embodiments comprise the identifier being a type of animal, such as the example of a system having four treatment device identified as alligator, badger, cat, and dog. In this specific example, the initials of the animals form an alphabetic sequence. Another embodiment in which the initials form a sequence is the identifiers being selected from radio code words such as the International Civil Aviation Organization (ICAO) code words Alpha, Bravo, Charlie, and Delta. In some embodiments, the identifier is printed onto the treatment device e.g. pad printing on the handle, cable, hub, connectors or other component. In some alternative embodiments, the identifier is an image other than alphanumeric characters (e.g. a symbol) which is printed on a treatment device.

In some embodiments, the visual indicator is permanent, for example a label, or other component which remains attached to the treatment device. In some alternative embodiments, the visual marker is detachable.

In alternative embodiments, the visual indicator is transient, for example an LED, or other device component which may be activated at one time or multiple times before or during a treatment procedure. In some such embodiments, an LED (an active visual identifier) activates once the treatment starts and deactivates upon completion of the treatment.

In some such embodiments, the LED (or some other type of light) becomes active once the treatment device is connected to the treatment source.

In other embodiments, the LED (or some other type of light) becomes active only after a user interacts with the treatment source to activate the visual identifier.

In another broad aspect of the invention, the system or treatment source comprises a user interface, and the user interface is operable to cooperate with one or more treatment devices which the user interface is in communication with to provide a matching identification to the user on the user interface corresponding to the visual identification (i.e. the device visual identifier) provided by the treatment device. In some embodiments, the treatment source comprises the user interface. The user interface typically includes a screen. The user interface typically includes an information display which comprises portions which correspond with the treatment devices. In such embodiments, a device identifier is displayed in a corresponding portion of the information display.

As a feature of this aspect, the interface may be colour coded to distinguish one treatment device from others, and this colour coding may correspond to the colour of a device visual identifier marker (e.g. an LED) associated with the respective treatment device. In some embodiments, each treatment device has a cable with a plurality of coloured LEDs which correspond with the colour coding of the interface. Some embodiments comprise the treatment device having a button which lights in the same colour (or approximately the same colour) as a colour associated with the corresponding portion of the interface screen.

Some alternative embodiments of the treatment device include a button, mechanical switch (e.g. a toggle or a slider), or pressure sensor which the use of causes a portion of the information display corresponding to the treatment device to brighten, flash, or otherwise alert the user.

In alternative embodiments, the interface includes an I/O component, such as one or more physical or virtual buttons, and the treatment source is operable to activate a visual indicator on a connected treatment device when a user interacts with the respective I/O component.

In further embodiments, the device visual identifier associated with a particular treatment device is operable to flash or blink (i.e. emit light) if an error, or other status change is detected, which is associated with that treatment device. The error may concurrently be displayed on the interface.

Embodiments of the present invention are operable to offer the user visual identification of one or more treatment devices connected to a treatment source. This would allow the user, for example, to make adjustments throughout the procedure in situations of errors, such as high impedance due to poor contact with tissue, etc.

In a third broad aspect, embodiments of the present invention comprise a system, the system comprising: an energy source for use with at least two treatment devices, the energy source being operable to be connected to the at least two treatment devices; and an information display associated with the energy source, the information display being operable to provide information about at least one device of the at least two treatment devices when the at least one device is connected to the energy source. The information display is configured to provide an association between a device identifier associated with the at least one device with information provided on the information display about the at least one device. In some embodiments the energy source comprises an electrosurgical generator. In other embodiments, the energy source comprises a battery.

As a feature of this broad aspect, the energy source comprises at least two channels which are operable to be connected to the at least two treatment devices wherein at least one of the at least two channels is associated with a portion of the information display which corresponds with the at least one device connected to the one of the at least two channels. Some embodiments further comprise a cable and a cable connector for connecting the at least one device to one of the at least two channels, wherein the device identifier associated with the at least one device comprises an identifying colour and wherein a portion of the cable connector to which the at least one device is coupled comprises the identifying colour. In some such embodiments, the system further comprises a generator hub which is connected to the energy source, and the cable connector being configured for connecting to the generator hub. In other such embodiments, the energy source comprises a port and the cable connector is configured for connecting to the port.

As another feature of this broad aspect, the at least two treatment devices comprise electrosurgical probes. In some embodiments, the at least two treatment devices comprise four electrosurgical probes.

In some embodiments of the third broad aspect, the device identifier comprises alphanumeric text. Some such embodiments have a device identifier which comprises a word. In some examples, the device identifier comprises a radio code word. In some such examples, the energy source is operable to be connected to four treatment devices which are associated with a plurality of radio code words comprised of Alpha, Bravo, Charlie, and Delta.

In some embodiments of the third broad aspect, the device identifier comprises a symbol.

In some embodiments of the third broad aspect, the device identifier comprises a coloured component, and the information display is operable to display a corresponding colour when the at least one device is connected to the energy source. Some such embodiments have a device identifier which comprises a coloured label.

Some embodiments comprise input means for a user to enter information for identifying one of the at least two treatment devices.

In some embodiments of the third broad aspect, the device identifier comprises an active visual identifier. In some such embodiments, the active visual identifier is a light-emitting diode. In some examples, the active visual identifier becomes active once the one of the at least two treatment devices is connected to the energy source and wherein the information display is operable to display an indication when the one of the at least two treatment devices is connected to the energy source. In other examples, the active visual identifier becomes active once a user interacts with the energy source to activate the device identifier. In some embodiments, the active visual identifier associated with the at least one device changes if the system produces an error or an alert associated with the at least one device. In some embodiments, the active visual identifier associated with the at least one device is activated when a treatment procedure is initiated using the at least one device.

In some embodiments, the device identifier comprises at least one etched character. Some embodiments comprise the device identifier being an image printed on the at least one device of the at least two treatment devices. In some embodiments, the device identifier is detachable from the at least one device.

As a feature of the third broad aspect, the system further comprises a user interface which includes the information display. In typical examples of this feature, the energy source includes the user interface. In some such examples, the user interface includes a screen. In some cases, the screen comprises a graphical user interface. In some examples, the screen comprises a touch screen. In some embodiments of this feature, the information display is operable to display the device identifier corresponding to the at least one device coupled to the energy source. In some embodiments, the device identifier comprises an active visual identifier which is operable to emit light when a user interacts with a component of the user interface. In some embodiments, wherein portions of the user interface are colour coded to correspond respectively to a colour of the device identifier associated with the at least one device connected to the energy source. In some examples, the active visual identifier comprises a light-emitting diode. In some embodiments, the device identifier is operable to emit light to thereby provide feedback to a user if a status change is detected for the at least one device with which the device identifier is associated.

Some embodiments of the system comprise an additional screen which is separate from the energy source. Some embodiments of the system comprise a single screen which is separate from the energy source.

Some embodiments having an information display, further comprise a barcode reader, and the device identifier comprises a barcode, and the barcode reader is operable to read the barcode and communicate the device identifier to the user interface to be displayed on the information display.

In some embodiments having an information display, the information display is configured to comprise at least two portions which correspond with the at least two treatment devices. In some such embodiments, the device identifier is displayed in a corresponding portion of the information display.

Some embodiments comprise a mechanical component which a user moves to thereby display an identifying colour for the at least one device and wherein the information display is operable to display a corresponding colour when the at least one device is connected to the energy source.

In some embodiments having a user interface, the device identifier comprises a label, and the system is operable to display a text of the label in a portion of the user interface corresponding to the at least one device with which the label is associated. In other embodiments, the device identifier comprises a label and a shape or symbol on the label is displayed in a portion of the user interface corresponding to the at least one device with which the label is associated. In some embodiments, the at least one device comprises an EEPROM and wherein the EEPROM includes unique identifying information programmed into the EEPROM. In some such embodiments, the system is operable to display identifying information in a portion of the user interface corresponding to the at least one device which comprises the EEPROM. In some examples, the at least one device is operable to produce a device auditory signal and wherein the information display is operable to indicate which treatment device is producing the device auditory signal. In some such examples, the at least one device comprises a speaker.

In some examples of the third broad aspect, the device identifier comprises a liquid crystal display. In other examples, the device identifier comprises a motion sensor which detects movement to thereby produce movement data which is communicated to the energy source for displaying on the information display. In some examples, the device identifier comprises a thermo-electric generator which is operable to produce an electrical signal using heat of a user's hand or a patient's body wherein the electric signal is communicated to the energy source for displaying on the information display. In some examples, the device identifier comprises a piezoelectric generator which can produce an electrical signal using pressure on the one of the at least two treatment devices wherein the electric signal is communicated to the energy source for displaying on the information display. In some examples, the at least one device comprises a thermochromatic portion which, when subjected to heat, changes to a colour for identifying the at least one device and wherein the information display is operable to display a corresponding colour when the at least one device is connected to the energy source. In some examples, the device identifier comprises a mechanical switch, and a corresponding portion of the information display indicates when the mechanical switch associated with the at least one device is actuated. In some examples, the at least one device comprises a pressure sensor, and wherein the information display is operable to provide an indication when pressure is applied to the pressure sensor.

In a fourth broad aspect, embodiments of the present invention comprise a system, the system comprising: an energy source and at least two treatment devices, the energy source having at least two channels, wherein at least one device of the at least two treatment devices is connected to at least one channel of the at least two channels and wherein the at least one device comprises a device identifier which corresponds with the at least one channel of the at least two channels.

As a feature of this broad aspect, the energy source comprises an electrosurgical generator.

As a feature of this broad aspect, the energy source comprises four channels.

As a feature of this broad aspect, the at least two treatment devices comprise electrosurgical probes. In some embodiments, the at least two treatment devices comprise four electrosurgical probes.

Some embodiments of the fourth broad aspect further comprise a cannula for introducing the at least one device into a patient's body, and an identifying colour being associated with the at least one device, wherein the cannula is comprised of a colour matching the identifying colour. Some such embodiments further comprise a user interface screen which includes an information display and in which a portion of the user interface screen corresponds with the at least one device, wherein the portion of the user interface screen is comprised of a colour matching the identifying colour.

In a fifth broad aspect, embodiments of the present invention comprise a system, the system comprising: an energy source; at least two treatment devices operable to be connected to the energy source; and an information display being operable to provide information about at least one device of the at least two treatment devices when the at least one device is connected to the energy source. The information display is configured to provide an association between a device identifier associated with the at least one device with information provided on the information display about the at least one device.

As a feature of the fifth broad aspect, the energy source has a single output, and the system includes a generator hub operable to be connected to the single output of the energy source, wherein the generator hub includes a plurality of ports for connecting to the at least two treatment devices.

BRIEF DESCRIPTION OF THE DRAWINGS

In order that the invention may be readily understood, embodiments of the invention are illustrated by way of examples in the accompanying drawings, in which.

DETAILED DESCRIPTION

Figures 1, 2:
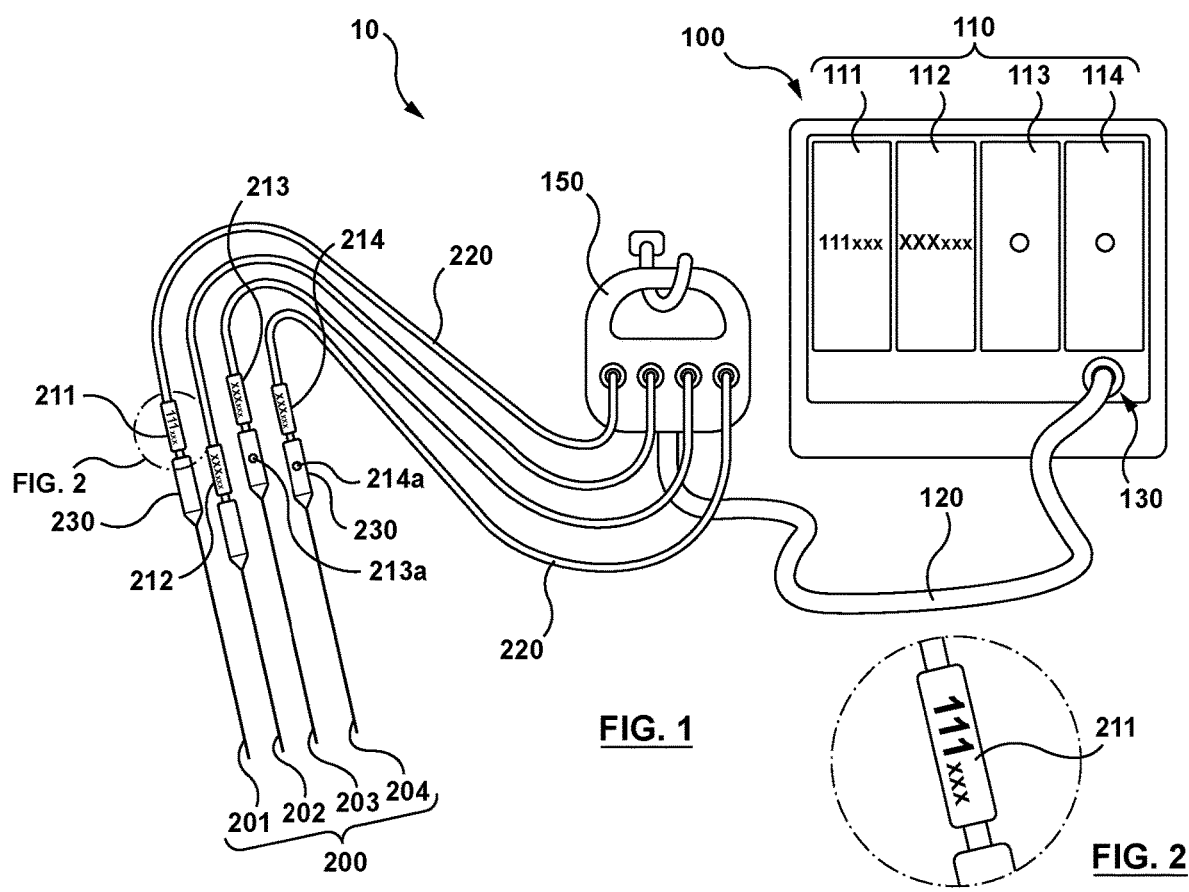
FIG. 1 is an illustration of an embodiment of a system of the invention.
FIG. 2 is an enlarged view of a portion of FIG. 1 indicated by dashed line.

During a radio frequency ablation treatment for pain, the user (e.g. an interventional radiologist, surgeon or equivalent) will often treat more than one tissue site at a time. For this reason, commercially available RF Pain Management systems are often capable of running up to four standard RF probes at one time. However, as the cables extend several feet between the probes and generator (probe tips are inside the sterile field while the generator is outside of the sterile field) this scenario can cause confusion as to which probe is connected to which channel of the RF generator. Typically the probes are identical or similar in appearance, further adding to the challenge of keeping track of which probe is connected to which channel. This can be especially troublesome if, during a treatment, one channel of the generator is showing high impedance or another error. In more severe cases, the patient could experience pain at one site and the physician may be forced to halt treatment at all sites as they cannot determine which probe corresponds to which channel on the generator.

In addition, a pain management radiofrequency-based system may offer a 'smart' detect feature which allow the generator to load treatment parameters or probe model when the probe is plugged in; However, after all probes are plugged in the user would typically not have an easy way of recalling which probe corresponds to which channel and, therefore, which treatment profile is associated with which probe.

Thus, there is a need for identifying individual treatment devices connected to a treatment source (e.g. an energy source). The present inventors have conceived of and reduced to practice embodiments of a system which enables a practitioner to determine correspondence between a plurality of treatment devices and channels of a treatment source. The system includes each treatment device having a visual identifier which corresponds with a treatment source channel. A device identifier is something that facilitates the identification of a treatment device. A typical embodiment of the system comprise an energy source and an information display associated with the energy source, the information display being operable to provide information about at least one of the treatment devices when the device is connected to the energy source. The information display is configured to provide an association between a device identifier associated with the treatment device with information provided on the information display about the device. In some embodiments the treatment source is a power supply and the treatment devices are electrosurgical probes. Treatment sources include electrical generators, batteries, fluid sources, and fluid withdrawal units. In general, a treatment source is any source of energy or the like that may be used in a medical procedure which may or may not provide actual treatment.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

FIG. 1 illustrates an embodiment of a system 10, the system including a generator 100 and a plurality of treatment devices 200. In the illustrated embodiment, the treatment devices 200 comprise radiofrequency probes.

Generator 100 includes a graphical user interface, GUI 110, a device cable 120 and a connector port 130 to which the cable may be releasably coupled.

The GUI is operable to display treatment parameters, information, etc. associated with the plurality of treatment devices 200 coupled to the generator 100.

In the illustrated example, there are four treatment devices, 201, 202, 203 and 204 coupled to the generator 100 via respective sterile cables 220, the cables 220 being coupled to device cable 120, for example via a cable hub 150. GUI 110 correspondingly displays information in GUI regions 111, 112, 113 and 114 corresponding to the respective treatment devices.

Alternatively, each treatment device may be connected individually to one of a plurality of connectors associated with the generator 100. The identifying function of the invention is particularly useful when used with systems having a hub since it is typical of such systems all on the probes are connected to the generator via a single cable connecting the hub to the generator i.e. there is no cable directly connecting a probe to a channel connector. Having a cable directly connecting a probe to a generator can aid a user in keeping track which channel a probe is connected to.

Each treatment device includes a feature providing identification of the treatment device.

For example, treatment device 203 includes a device identifier comprising an active visual identifier 213a such as an LED (or some other type of light) which is operable to flash or blink (i.e. emit light) when a user interacts with an I/O component (e.g. a physical or virtual button, knob or switch) in GUI region 113.

Some embodiments of treatment devices comprise a label displaying a serial number which also displays on the interface screen. Typically, a serial number is comprised of alphanumeric text. In some such embodiments, the serial number is in a colour matching a colour on the interface screen. Some embodiments include a shape or symbol on the label which is displayed in the corresponding part of the user interface screen.

In the illustrated example of FIG. 1, treatment devices 201, 202, 203, 204 include labels 211, 212, 213, 214, which are device visual identifiers. The system 10 is operable to display the text of, for example, label 211 in GUI region 111. Label 211 is shown in greater detail in FIG. 2. In some embodiments, a cable 220 is permanently attached to treatment device 201, and the label being attached to the device includes the label being attached to the handle 230, cable 220, or any other part of treatment device 201. In alternative embodiments, cable 220 is detachable and label 211 is attached to the cable i.e. label 211 is not directly attached to treatment device 201.

In some embodiments, the device visual identifier (e.g. a label) is a LCD (liquid crystal display). Some LCD labels also provide the temperature and/or the time. In some such embodiments, the LCD (liquid crystal display) is a colour LCD having a colour matching a colour on the user interface.

Some embodiments include each cable having a distinct appearance, such as cables having different colours, shape of cross-section, or patterns. Patterns can include geometric patterns such a polka dots, triangles, squares, tiling, fractals, etc. Non-geometric patterns could include wavy animal-style stripes, snake skin configurations, feathers, leaf shapes, flowers, wood grain contouring, etc. In some such embodiments the appearance of the cable corresponds with at least a portion the probe. In some other embodiments the appearance of each cable matches a corresponding portion of the user interface. In some embodiments, the cables have different shapes such as, for example, straight, wavy, helical, etc.

Furthermore, in the illustrated example, treatment device 203 includes an active visual identifier 213a comprising a light (e.g. an LED) operable to blink or flash when an error is associated with device treatment 203, the error being concurrently displayed in GUI region 113.

In some embodiments, additional information is integrated into the LED signal related to treatment status e.g. to alert a user when a lesion is fully formed. The user would be able to identify the probe whose lesion has been completed and to remove and replace it at another site to be treated.

In alternative embodiments, during treatment the GUI region 113 communicates treatment status to the user via the probe device 203 by blinking an active visual identifier 213a (e.g. an LED) in cases of errors such as high or low impedance, or high or low temperature. For example, a light on a probe which flashes if impedance exceeds 120% of starting impedance. This is useful during the delivery of therapeutic energy, or temperature monitoring during an ablation or cryoablation procedure.

In addition, when lesions are formed in sequence using treatment devices which are probes, (e.g., treatment device 201 starts, then treatment device 202, then treatment device 203, etc.), the user can begin placement of treatment device 201 for a second lesion without waiting for all probes to complete ablation with confidence that they are not disrupting a treatment in progress based on information provided in the corresponding GUI region and associated visual indicator that the treatment at that site has been completed. This could be useful during the delivery of therapeutic energy, or temperature monitoring during an ablation or a cryoablation procedure.

In addition, in the illustrated example, device 204 includes an active visual identifier 214a comprising a device visual identifier (e.g. an LED) having a particular colour, and the colour of the device visual identifier (e.g. an LED) corresponds to a colour being displayed in corresponding GUI region 114. In some alternative embodiments, the treatment devices include a thermochromatic portion which changes to the device's identifying colour when subjected to heat. The heat can be supplied by a patient's body, or alternatively, by energy delivered through the device whereby the device attains the identifying colour when active.

In the illustrated example, when the user plugs a treatment device such as a probe into the generator 100, the GUI 110 provides visual feedback on the screen related to probe model and default treatment parameters. The four channels on the GUI may be color coded, i.e., channel 1=red, channel 2=green, channel 3=blue, channel 4=orange, and, for example with respect to probe device 204, the generator 100 sends a corresponding forward voltage (or frequency value) to the connected probe device 204 which will turn the embedded active visual identifier 214a (e.g. an LED) the same color, i.e., active visual identifier 214a in probe device 204 turns orange, corresponding to the background color of channel 4 displayed in region 114, etc.

Alternatively, when probe device 202 is connected to the generator 100, the GUI 110 will load a unique probe name, or ID (the device visual identifier) which has been programmed into the EEPROM (electrically erasable programmable read-only memory) of the probe device 202. The user will be able to view the name in the corresponding channel GUI region 112, as well as on a label affixed to the device.

Some embodiments include means for the user to enter the serial number of the treatment devices, with such embodiments typically also including means to lock in the serial number (i.e. prevent the accidental changing of the number). Some of these embodiments have user selectable buttons for entering the serial number. Other embodiments of treatment devices have rollers or sliders for selecting a serial number.

Alternative systems include a barcode reader and each of the treatment devices having a barcode associated with the treatment device which includes the treatment device's identifier. The barcode reader is used to read treatment device's barcode and the identifier (e.g. a serial number) is sent to the system interface screen which displays the identifier. Typically, the serial number is displayed on screen in a colour which matches a colour associated with the barcode, for example, the barcode having a colored background or a colored strip beside the bars.

Some embodiments of treatment devices comprise a mechanical component such as a roller or slider (or other mechanical means) which the user moves to thereby display an identifying colour for the treatment device and wherein the information display is operable to display a corresponding colour when the treatment device is connected to the energy source.

Some embodiments of a treatment device which have a colored label (or some other component having an identifying colour) include the cable connector used for connecting the cable to a generator hub or directly into a generator comprising the same colour as the label (or other identifying coloured component) to clarify which channel a treatment device (probe) is connected into. In some embodiments the entire cable connector has the identifying colour, while in other embodiments, only a portion of the connector (e.g. the back-nut) has the identifying colour.

Some embodiments include a cannula which is used for introducing a treatment device being comprised of an identifying colour matching a colour associated with the label (or treatment device) and/or a colour associated with the corresponding portion of the user interface screen. In use, a user would match the appropriate coloured treatment device to the cannula and the cannula to the corresponding channel of the treatment source. Some such embodiments include a set of colour coded probes and corresponding colour coded cannulas wherein a treatment device is configured such that it can only be inserted into the matching cannula e.g. a set wherein a blue probe can be inserted into a blue cannula but not a red cannula.

In addition to a visual signal, some embodiments include an auditory signal could be used to indicate which probe is connected to which channel at initiation, or if probe status update was required. For example, a probe (a treatment device) could produce an auditory signal which corresponds with another auditory signal which is produced by a user interface, or the user interface could indicate which treatment device is producing the auditory signal by some visual means, for example with a light or a graphical symbol. In such examples, the light or a graphical symbol cold be flashing. In general, a device identifier is something that facilitates the identification of a treatment device.

The different embodiments of the visual identification provided by/on the treatment device described above can be combined together. For example, the use of colour or auditory signals can be combined with alphanumeric characters, symbols, LEDs, printed and etched characters. Other combinations are readily implementable.

Monitoring of a treatment procedure can include using auditory feedback to provide information to the user. Some such embodiments include the treatment device having a speaker e.g. a speaker in the handle of a probe. Other such embodiments include the treatment source having a speaker e.g. a generator having a speaker. Alternative embodiments include feedback being provided to the surgeon by vibrations from the treatment device e.g. from the handle of a probe.

Other embodiments include the treatment device comprising motion sensors for providing feedback to the surgeon. For example, a probe having a motion sensor which detects movement to produce movement data and the movement data being communicated to a surgical generator.

Some embodiments of the treatment device can generate power when handled by a user whereby a signal for identifying the treatment device can be sent to the treatment source (e.g. a generator) and/or the interface screen. Some such embodiments comprise a thermo-electric generator which can produce an electrical signal using the heat of the operator's hand and/or the patient's body. Some other embodiments comprise a piezoelectric generator which can produce an electrical signal using the pressure created by the operator's hand gripping the treatment device and/or the treatment device being pressed against patient's body. Other embodiments comprise a battery and a heat sensor or a pressure sensor.

Some embodiments of the system comprise the interface screen displaying patient anatomy wherein the screen indicates the position of a probe which is plugged in, and the screen's map of the anatomy identifies the probes.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A system comprising:
   an energy source for use with at least two treatment devices, the energy source being operable to be connected to the at least two treatment devices at a same time; and
   an information display associated with the energy source, the information display being operable to provide information about the at least two treatment devices when the at least two treatment devices are connected to the energy source,
   wherein the information display is configured to provide an association between a first device identifier associated with and connected to a first treatment device of the at least two treatment devices with first information provided on the information display about the first treatment device and an association between a second device identifier associated with and connected to a second treatment device of the at least two treatment devices with second information provided on the information display about the second treatment device, wherein both the first device identifier and the second device identifier are distinct from the information display and directly identifiable by a user, wherein the first device identifier comprises a first active visual identifier on the first treatment device, wherein the second device identifier comprises a second active visual identifier on the second treatment device, and wherein each of the first active visual identifier and the second active visual identifier is configured to indicate an operational status change of the respective first treatment device or second treatment device.

2. The system of claim 1, wherein the energy source comprises an electrosurgical generator and the at least two treatment devices comprise electrosurgical probes.

3. The system of claim 1, wherein the energy source comprises at least two channels which are operable to be connected to the respective at least two treatment devices, and wherein the at least two channels are associated with a respective portion of the information display which corresponds with a respective treatment device of the at least two treatment devices connected to a respective channel of the at least two channels.

4. The system of claim 3, further comprising a cable and a cable connector for connecting the at least two treatment devices to a respective one of the at least two channels, wherein the first device identifier associated with the first treatment device comprises an identifying colour and wherein a portion of the cable connector to which the first treatment device is coupled comprises the identifying colour.

5. The system of claim 4, wherein the system further comprises a generator hub which is connected to the energy source, and the cable connector being configured for connecting to the generator hub.

6. The system of claim 1, wherein the device identifier comprises alphanumeric text.

7. The system of claim 1, wherein the device identifier comprises a symbol.

8. The system of claim 1, wherein the device identifier comprises a coloured component and wherein the information display is operable to display a corresponding colour when the at least one device is connected to the energy source.

9. The system of claim 1, further comprising input means for a user to enter information for identifying one of the at least two treatment devices.

10. The system of claim 1, wherein the first active visual identifier comprises a first light, and wherein the second active visual identifier comprises a second light.

11. The system of claim 10, wherein the first active visual identifier associated with the first treatment device is configured to change in response to the system producing an error or an alert associated with the first treatment device.

12. The system of claim 10, wherein the first active visual identifier associated with the first treatment device is configured to activate in response to a treatment procedure being initiated using the first treatment device.

13. The system of claim 1, wherein the first active visual identifier is configured to emit light in response to the first treatment device being connected to the energy source, and wherein the information display is operable to display an indication when the first treatment device is connected to the energy source.

14. The system of claim 1, wherein the first active visual identifier becomes active in response to a user interacting with the energy source to activate the device identifier.

15. The system of claim 1, further comprising a user interface which includes the information display.

16. The system of claim 15, wherein the energy source includes the user interface.

17. The system of claim 15, wherein the information display is operable to display the first information that corresponds to the first device identifier associated with the first treatment device coupled to the energy source and display the second information that corresponds to the second device identifier associated with the second treatment device coupled to the energy source.

18. The system of claim 15, wherein at least the first active visual identifier is operable to emit light in response to a user interacting with a component of the user interface.

19. The system of claim 15, wherein the first treatment device is operable to produce a device auditory signal, and wherein the information display is operable to indicate that the first treatment device is producing the device auditory signal.

20. The system of claim 1, wherein the first treatment device comprises a thermochromatic portion which, when subjected to heat, changes to a colour for identifying the first treatment device, and wherein the information display is operable to display a corresponding colour when the first treatment device is connected to the energy source.

21. The system of claim 1, further comprising a mechanical component which a user moves to thereby display an identifying colour for the first treatment device, and wherein the information display is operable to display a corresponding colour when the first treatment device is connected to the energy source.

22. The system of claim 1, wherein the first active visual identifier is operable to emit light to provide feedback to a user in response to a status change detected for the first treatment device with which the first active visual identifier is associated.

23. The system of claim 1, wherein the first device identifier comprises a motion sensor configured to detect movement and produce movement data which is communicated to the energy source for displaying on the information display.

24. The system of claim 1, wherein the first device identifier comprises a thermo-electric generator operable to produce an electrical signal using heat of a user's hand or a patient's body, and wherein the electric signal is communicated to the energy source for displaying on the information display.

25. The system of claim 1, wherein the first device identifier comprises a piezoelectric generator configured to produce an electrical signal using pressure on the first treatment device, wherein the electric signal is communicated to the energy source for displaying on the information display.

26. A system comprising:
an energy source; and
at least two treatment devices, wherein the energy source comprises at least two channels, wherein a first treatment device of the at least two treatment devices is configured to be connected to a first channel of the at least two channels and a second treatment device of the at least two treatment devices is configured to be connected to a second channel of the at least two channels, wherein the first treatment device comprises a first device identifier which corresponds with the first channel of the at least two channels, and wherein the second treatment device comprises a second device identifier which corresponds with the second channel of the at least two channels, wherein both the first device identifier and the second device identifier are distinct from an information display associated with the energy source and directly identifiable by a user, wherein the first device identifier comprises a first active visual identifier on the first treatment device, wherein the second device identifier comprises a second active visual identifier on the second treatment device, and wherein each of the first active visual identifier and the second active visual identifier is configured to indicate an operational status change of the respective first treatment device or second treatment device.

27. The system of claim 26, wherein the energy source comprises an electrosurgical generator, and wherein the at least two treatment devices comprise electrosurgical probes.

28. The system of claim 26, further comprising a cannula configured to introduce the first treatment device into a patient's body, wherein an identifying colour is associated with the first treatment device, and wherein the cannula comprises a colour matching the identifying colour.

29. The system of claim 28, further comprising a user interface screen comprising the information display and in which a portion of the user interface screen corresponds with the first treatment device, wherein the portion of the user interface screen comprises a colour matching the identifying colour.

30. A system comprising:
an energy source;
at least two treatment devices operable to be connected to the energy source at the same time; and
an information display being operable to provide information about the at least two treatment devices when the at least two treatment devices are connected to the energy source;
wherein the information display is configured to provide an association between a first device identifier associated with and connected to a first treatment device of the at least two treatment devices with first information provided on the information display about the first treatment device and an association between a second device identifier associated with and connected to a second treatment device of the at least two treatment devices with second information provided on the information display about the second treatment device, wherein both the first device identifier and the second device identifier are distinct from the information display and directly identifiable by a user, wherein the first device identifier comprises a first active visual identifier on the first treatment device, wherein the second device identifier comprises a second active visual identifier on the second treatment device, and wherein each of the first active visual identifier and the second active visual identifier is configured to indicate an operational status change of the respective first treatment device or second treatment device.

31. The system of claim 30, wherein the energy source has a single output, and wherein the system comprises a generator hub operable to be connected to the single output of the energy source, and wherein the generator hub includes a plurality of ports for connecting to respective devices of the at least two treatment devices.

* * * * *